United States Patent [19]

Sattler et al.

[11] Patent Number: 5,023,251

[45] Date of Patent: Jun. 11, 1991

[54] O/W CREAM CONTAINING HYDROCORTISONE DIESTER

[75] Inventors: Henning Sattler, Hamburg; Bodo Asmussen, Ammersbek, both of Fed. Rep. of Germany

[73] Assignee: Beiersdorf AG, Hamburg, Fed. Rep. of Germany

[21] Appl. No.: 429,735

[22] Filed: Oct. 31, 1989

Related U.S. Application Data

[63] Continuation of Ser. No. 904,539, Sep. 5, 1986, abandoned.

[30] Foreign Application Priority Data

Sep. 28, 1985 [DE] Fed. Rep. of Germany ....... 3534743

[51] Int. Cl.$^5$ ............................................ A61K 31/575
[52] U.S. Cl. .................................... 514/179; 514/180
[58] Field of Search ........................................ 514/179

[56] References Cited

U.S. PATENT DOCUMENTS 4,333,927  6/1982  Ofuchi ................................ 514/179

FOREIGN PATENT DOCUMENTS 47604    5/1979  Australia .
009856   6/1904  European Pat. Off. .
131821   1/1985  European Pat. Off. .
253999   8/1984  France .
253999   8/1984  France .

OTHER PUBLICATIONS

Merck Index, 10th Ed., pp. 144, 693–694, 1983.
Kawasima Chem. Abstracts, vol. 103, 1985, p. 258.
Preface, Library of Congress Cataloging in Publication Data, Flick, Ernest W., p. 213.

*Primary Examiner*—Mark L. Berch
*Attorney, Agent, or Firm*—Sprung Horn Kramer & Woods

[57] ABSTRACT

The invention relates to a cream containing hydrocortisone diester, which contains
0.01–0.5% of hydrocortisone diester
5–20% of O/W emulsifier based on polyoxyethylene fatty acid esters and fatty alcohols
0–10% of stearyl alcohol
1–50% of white vaseline
0–5% of benzyl alcohol and
20–80% of water.

2 Claims, No Drawings

O/W CREAM CONTAINING HYDROCORTISONE DIESTER

This is a continuation of application Ser. No. 904,539, filed Sept. 5, 1986, now abandoned.

The present invention relates to a new O/W cream which contains hydrocortisone diester.

An oily ointment or fatty ointment containing the active ingredient hydrocortisone 17-butyrate 21-propionate has already been disclosed in German Offenlegungsschrift 3,402,877.

Ointments whose water content is zero or only very low do not form emulsions, and thus are not creams. Formulations of this type are not always satisfactory in respect of absorption of active ingredient. Moreover, inconveniences are associated with their use.

Furthermore, an O/W cream containing the active ingredient hydrocortisone 17-butyrate 21-propionate is disclosed in German Offenlegungsschrift 3,402,880.

However, the cream base described has not always proved satisfactory, especially in respect of storage stability, that is to say the stability of the content of active ingredient. This particularly applies to the case where hydrocortisone diesters other than the diester described in this citation are used with the specified base.

The object of the invention is to provide an O/W cream which contains a hydrocortisone diester and which ensures satisfactory storage stability and high absorption of the active ingredient through the skin. The particular intention is to produce an O/W cream which contains hydrocortisone 17-propionate 21-acetate and has these properties.

This object is achieved by an O/W cream which is characterized in that it contains
0.01–0.5 % of hydrocortisone diester
5–20 % of O/W emulsifier based on polyoxy-ethylene fatty acid esters and fatty alcohols
0–10 % of stearyl alcohol
1–50 % of white vaseline
0–5 % of benzyl alcohol and
20–80 % of water.

The O/W cream preferably contains
0.025–0.2 % of hydrocortisone diester
7.5–15 % of O/W emulsifier based on polyoxy-ethylene fatty acid esters and fatty alcohols
0.1–5 % of stearyl alcohol
5–25 % of white vaseline
0.1–3 % of benzyl alcohol and
30–70 % of water
but in particular
0.13% of hydrocortisone diester
12.5 % of O/W emulsifier based on polyoxy-ethylene fatty acid esters and fatty alcohols
3.5 % of stearyl alcohol
15 % of white vaseline
2.2 % of benzyl alcohol and
66.67% of water.

All the stated amounts, proportions and percentages are based on weight.

Suitable hydrocortisone diesters are known and are specified in, for example, German Offenlegungsshriften 2,910,899 and 2,826,257. Preferred esters are hydrocortisone 17-propionate 21-acetate, hydrocortisone 17-butyrate 21-acetate, hydrocortisone 17,21-dipropionate, hydrocortisone 17-propionate 21-butyrate, and hydrocortisone 17-butyrate 21-propionate.

Very particularly preferred O/W cream formulations according to the invention are those containing hydrocortisone 17 alpha-propionate 21-acetate as main active ingredient.

They are distinguished by particularly high storage stability and high efficacy. Even after storage for several years there is virtually no measurable decrease in the content of active ingredient.

The fatty alcohol contribution to the O/W emulsifier is preferably formed of higher fatty alcohols. Emulsifiers described in the literature (Lexikon der Hilfsstoffe fur Pharmazie, Kosmetik und angrenzende Gebiete (Lexicon of auxiliaries for pharmacy, cosmetics and related areas), H. P. Fiedler, 1971 and 1981, Editio Cantor Aulendorf) are commercially available under the tradenames Crodawax and Polawax (supplied by Croda, Germany). Crodawax GP200 is preferred.

The cream preferably contains stearyl alcohol and benzyl alcohol as preservative in the specified amounts.

In addition, it is possible for smaller proportions of additives such as glycerol, propylene glycol, isopropyl fatty acid esters, such as isopropyl myristate and isopropyl palmitate, waxes, for example hydrocarbon waxes, such as ozokerite, and beeswax and spermaceti and their substitutes, as well as agents for controlling the pH, although these are not generally necessary in the cream according to the invention, to be present.

The new cream according to the invention provides an O/W cream which contains a hydrocortisone diester, in particular hydrocortisone 17-propionate 21-acetate, and which is distinguished by high efficacy and high storage stability.

To prepare the cream, the constituents of the fatty phase, vaseline, emulsifier and stearyl alcohol are melted and brought to 60–80° C. Water is likewise heated to 60–80° C. and is mixed with the fatty phase. The active ingredient hydrocortisone diester is added at about 60° C. The composition is stirred while it is allowed to cool to about 40° C., and the preservative benzyl alcohol is added. The composition is stirred further while allowing it to cool and solidify.

The active ingredient is very efficiently absorbed from the cream according to the invention, which has an outstanding storage stability. It is used for the treatment of eczemas, dermatitis, psoriasis and inflammations.

To cure or treat these disorders, the cream according to the invention can be applied topically to the lesions. The amount of cream which is applied varies in accordance with the concentration of the active active ingredient in the cream. In general, a suitable amount is applied to the lesion several times a day, depending on the severity of the disorder which is to be treated.

The examples which follow serve to illustrate the invention:

EXAMPLE 1

An O/W cream is prepared with the specified constituents:

| | |
|---|---|
| hydrocortisone 17-propionate 21-acetate | 0.127 g |
| O/W emulsifier based on polyoxyethylene fatty acid esters and fatty alcohols (Crodawax GP 200) | 12.500 g |
| stearyl alcohol | 3.500 g |
| white vaseline | 15.000 g |
| benzyl alcohol | 2.200 g |
| purified water | 66.673 g |

-continued

|   |   |
|---|---|
|   | 100.000 g |

The vaseline, stearyl alcohol and emulsifier are heated to 75° C. and mixed with water at the same temperature. After the composition has cooled to about 60° C., the hydrocortisone 17-propionate 21-acetate is added, and stirring is continued until cold, the benzyl alcohol being added at about 40° C.

EXAMPLE 2

An O/W cream is prepared with the specified constituents:

| hydrocortisone 17-propionate 21-acetate | 0.100 g |
|---|---|
| O/W emulsifier based on polyoxyethylene fatty acid esters and fatty alcohols (Crodawax GP 200) | 8.0 g |
| stearyl alcohol | 8.0 g |
| white vaseline | 20.0 g |
| benzyl alcohol | 2.200 g |
| purified water | 61.7 g |
|   | 100.000 g |

The vaseline, stearyl alcohol and emulsifier are heated to 75° C. and mixed with water at the same temperature. After the composition has cooled to about 60° C., the hydrocortisone 17-propionate 21-acetate is added, and stirring is continued until cold, the benzyl alcohol being added at about 40° C.

EXAMPLE 3

An O/W cream is prepared with the specified constituents:

| hydrocortisone 17-propionate 21-acetate | 0.05 g |
|---|---|
| O/W emulsifier based on polyoxyethylene fatty acid esters and fatty alcohols (Crodawax GP 200) | 15.0 g |
| white vaseline | 15.000 g |
| benzyl alcohol | 1.5 g |
| purified water | 68.45 g |
|   | 100.000 g |

The vaseline and emulsifier are heated to 75° C. and mixed with water at the same temperature. After the composition has cooled to about 60° C., the hydrocortisone 17-propionate 21-acetate is added, and stirring is continued until cold, the benzyl alcohol being added at about 40° C.

EXAMPLE 4

An O/W cream is prepared with the specified constituents:

| hydrocortisone 17-butyrate 21-propionate | 0.127 g |
|---|---|
| O/W emulsifier based on polyoxyethylene fatty acid esters and fatty alcohols (Crodawax GP 200) | 12.500 g |
| stearyl alcohol | 3.500 g |
| white vaseline | 15.000 g |
| benzyl alcohol | 2.200 g |
| purified water | 66.673 g |
|   | 100.000 g |

The vaseline, stearyl alcohol and emulsifier are heated to 75° C. and mixed with water at the same temperature. After the composition has cooled to about 60° C., the hydrocortisone 17-butyrate 21-propionate is added, and stirring is continued until cold, the benzyl alcohol being added at about 40° C.

EXAMPLE 5

An O/W cream is prepared with the specified constituents:

| hydrocortisone 17-butyrate 21-acetate | 0.127 g |
|---|---|
| O/W emulsifier based on polyoxyethylene fatty acid esters and fatty alcohols (Crodawax GP 200) | 12.500 g |
| stearyl alcohol | 3.500 g |
| white vaseline | 15.000 g |
| benzyl alcohol | 2.200 g |
| purified water | 66.673 g |
|   | 100.000 g |

The vaseline, stearyl alcohol and emulsifier are heated to 75° C. and mixed with water at the same temperature. After the composition has cooled to about 60° C., the hydrocortisone 17-butyrate 21-acetate is added, and stirring is continued until cold, the benzyl alcohol being added at about 40° C.

We claim:
1. A cream consisting essentially of
0.13% of hydrocortisone 17-propionate 21-acetate,
12.5% of O/W emulsifier based on Crodawax,
3.5% of stearyl alcohol,
15% of white vaseline,
2.2% of benzyl alcohol, and
66.67% of water.
2. A cream according to claim 1, wherein the O/W emulsifier is based on Crodawax GP 200.

* * * * *

UNITED STATES PATENT AND TRADEMARK OFFICE
CERTIFICATE OF CORRECTION

PATENT NO. : 5,023,251

DATED : June 11, 1991

INVENTOR(S) : Sattler et al.

It is certified that error appears in the above-identified patent and that said Letters Patent is hereby corrected as shown below:

Title page, under item [56] References Cited:

FOREIGN PATENT DOCUMENTS: Delete " 009856, 6/1904 " and substitute -- 0098566, 1/1984 --; delete " 253999 " and substitute -- 2539991 --; delete " 253999 " and substitute -- 2539992 --; insert -- 2851544, 6/1980, Fed. Rep. of Germany --.

Signed and Sealed this

Twenty-fifth Day of May, 1993

Attest:

MICHAEL K. KIRK

*Attesting Officer*     Acting Commissioner of Patents and Trademarks